US006822001B2

(12) United States Patent
Schwendner et al.

(10) Patent No.: US 6,822,001 B2
(45) Date of Patent: Nov. 23, 2004

(54) COMBINATION THERAPY USING PENTAFLUOROBENZENESULFONAMIDES AND ANTINEOPLASTIC AGENTS

(75) Inventors: Susan Schwendner, San Bruno, CA (US); Pieter Timmermans, Redwood City, CA (US); Jacqueline Walling, Burlingame, CA (US)

(73) Assignee: Tularik Inc., South San Francisco, CA (US)

( * ) Notice: Subject to any disclaimer, the term of this patent is extended or adjusted under 35 U.S.C. 154(b) by 0 days.

(21) Appl. No.: 10/052,905

(22) Filed: Nov. 2, 2001

(65) Prior Publication Data

US 2002/0177548 A1 Nov. 28, 2002

Related U.S. Application Data

(60) Provisional application No. 60/245,878, filed on Nov. 3, 2000.

(51) Int. Cl.$^7$ ................. A61K 31/18; A61K 31/185; A61K 31/195; A61K 31/535
(52) U.S. Cl. ................ 514/601; 514/25; 514/27; 514/34; 514/44; 514/49; 514/117; 514/403; 514/404; 514/449; 514/471; 514/472; 514/479; 514/492; 514/588; 514/592; 514/593; 514/595; 514/596; 514/597; 514/598; 514/602; 514/603; 514/604; 514/605
(58) Field of Search ................ 514/601, 25, 27, 514/34, 44, 49, 117, 403, 404, 449, 471, 472, 479, 492, 588, 592, 593, 595–598, 602–605

(56) References Cited

U.S. PATENT DOCUMENTS

| | | | |
|---|---|---|---|
| 1,955,207 A | 4/1934 | Slotter et al. | |
| 2,358,365 A | 9/1944 | Tullar | |
| 2,402,623 A | 6/1946 | Hester et al. | |
| 2,450,863 A | 10/1948 | Altamura et al. | |
| 2,937,202 A | 5/1960 | Slagh et al. | |
| 3,034,955 A | 5/1962 | Frick et al. | |
| 3,322,828 A | 5/1967 | Muth et al. | |
| 3,505,455 A | 4/1970 | Gipstein et al. | |
| 3,951,910 A | 4/1976 | Mark | |
| 4,013,621 A | 3/1977 | Knell | |
| 4,034,110 A | 7/1977 | Mitrovic et al. | |
| 4,080,379 A | 3/1978 | Seng et al. | |
| 4,123,553 A | 10/1978 | Mitrovic et al. | |
| 4,239,699 A | 12/1980 | MacKay et al. | |
| 4,258,058 A | 3/1981 | Witte et al. | |
| 4,373,017 A | 2/1983 | Masukawa et al. | |
| 4,443,477 A | 4/1984 | Witte et al. | |
| 4,483,986 A | 11/1984 | Dominianni | |
| 4,692,466 A | 9/1987 | Yoshimoto et al. | |
| 4,851,445 A | 7/1989 | Yoshimoto et al. | |
| 4,870,107 A | 9/1989 | Yoshimoto et al. | |
| 4,881,969 A | 11/1989 | Saupe et al. | |
| 4,883,914 A | 11/1989 | Alvarado et al. | |
| 4,900,867 A | 2/1990 | Wilkes et al. | |
| 4,918,106 A | 4/1990 | Yoshimoto et al. | |
| 5,143,937 A | 9/1992 | Lang et al. | |
| 5,189,211 A | 2/1993 | Sato et al. | |
| 5,250,549 A | 10/1993 | Yoshino et al. | |
| 5,280,043 A | 1/1994 | Cooper et al. | |
| 5,385,931 A | 1/1995 | Bigg et al. | |
| 5,387,709 A | 2/1995 | Lardy et al. | |
| 5,464,826 A | 11/1995 | Grindley et al. | |
| 5,610,320 A | 3/1997 | Yoshino et al. | |
| 5,773,236 A | 6/1998 | Diwu et al. | |
| 5,780,483 A | 7/1998 | Widdowson et al. | |
| 5,880,151 A | 3/1999 | Medina et al. | |
| 5,891,917 A | 4/1999 | Tang et al. | |
| 6,121,304 A | 9/2000 | Flygare et al. | |
| 6,153,585 A | 11/2000 | Rubenstein et al. | |
| 6,211,167 B1 | 4/2001 | Houze | |
| 6,214,880 B1 | 4/2001 | Houze | |
| 6,284,923 B1 | 9/2001 | Medina et al. | |
| 6,316,484 B1 | 11/2001 | Flygare et al. | |
| 6,355,628 B1 * | 3/2002 | Schwender et al. | 514/117 |
| 6,465,448 B1 | 10/2002 | Gerson et al. | |
| 6,482,860 B1 * | 11/2002 | Flygare et al. | 514/602 |
| 6,528,513 B2 | 3/2003 | Cushing et al. | |
| 6,583,165 B2 | 6/2003 | Houze | |
| 6,630,513 B1 | 10/2003 | Rubenstein et al. | |
| 2002/0143036 A1 | 10/2002 | Flygare et al. | |
| 2003/0162817 A1 | 8/2003 | Flygare et al. | |
| 2003/0207864 A1 | 11/2003 | Houze | |
| EP | 0 472 449 A | 2/1992 | |
| EP | 0 472 053 A | 2/1999 | |

(List continued on next page.)

FOREIGN PATENT DOCUMENTS

| | | |
|---|---|---|
| DE | 622 494 C | 11/1935 |
| DE | 3535167 | 4/1987 |
| DE | 36 23 184 A | 1/1988 |
| DE | 3821540 | 12/1989 |
| EP | 0 391 799 A | 10/1990 |
| EP | 0 469 901 A | 2/1992 |

OTHER PUBLICATIONS

Fielding et al, "Synthesis and Reactions of 4–sulpho–2,3,5, 6–Tetrafluorobenzoic Acid"; *Journal of Fluorine Chemistry*, vol. 59, No. 1, pp. 15–31 (1992).

Raibekas et al. "Affinity Probing of Flavia Binding Sites. 2. Identification of Reactive cysteine in the Flavin Domain of *Escherichia coli* DNA Photolyase"; *Biochemistry*, vol. 33, No. 42, pp. 12656–12664 (1994).

Shealy et al. "2–Haloethylating Agents for Cancer Chemotherapy. 2–Haloethyl Sulfonates"; *Journal of Medicinal Chemistry*, vol. 26, pp. 1168–1173 (Aug. 1983).

(List continued on next page.)

Primary Examiner—Frederick Krass
(74) Attorney, Agent, or Firm—Townsend and Townsend and Crew LLP

(57) ABSTRACT

Combination therapies are provided for the treatment of proliferative disorders which use a pentafluorobenzenesulfonamide of formula I and an antineoplastic agent such as gemcitabine or paclitaxel.

26 Claims, 3 Drawing Sheets

U.S. PATENT DOCUMENTS

| | | |
|---|---|---|
| FR | 2456731 A | 12/1980 |
| GB | 859 345 A | 1/1961 |
| GB | 938 890 A | 10/1963 |
| GB | 1 189 720 A | 4/1970 |
| GB | 1 242 057 A | 8/1971 |
| GB | 1 306 564 A | 2/1973 |
| WO | WO 97/30677 | 8/1997 |
| WO | WO 98/05315 | 2/1998 |
| WO | WO 98/05315 A1 | 2/1998 |
| WO | WO 98/16227 A | 4/1998 |
| WO | WO 98/22101 A | 5/1998 |
| WO | WO 99/67258 A | 12/1999 |
| WO | WO 00/17159 A | 3/2000 |
| WO | WO 00/35865 | 6/2000 |
| WO | WO 00/61142 A1 | 10/2000 |
| WO | WO 00/73264 A | 12/2000 |
| WO | WO 01/08693 | 2/2001 |

OTHER PUBLICATIONS

Olander et al., "A Study of the binding of two sulfonamides to Carbonic Anhydrase"; *Journal of American Chemical Society*, vol. 95, No. 5, pp. 1616–1621 (Mar. 7, 1973).

Hawkinson, et al; "Studies of the Solvolysis of 2–Adamantyl Pentafluorobenzenesulfonate: A $Y_{PFBS}$ Scale"; *The Journal of Organic Chemistry*, Aug. 1988, vol. 53, No. 16, pp 3857–3860.

Chemical Abstracts, vol. 50, No. 1, Jan. 10, 1956 Columbus, Ohio, US; abstract No. 217g, V.O. Lukashevich: "Sulphonation of halogen–substituted benzene derivatives, formation of anhydrides of corresponding sulphonic acids" col. 217; XP002083056 see abstract & Doklady Akad. Nauk S.S.S.R., vol. 99, 1954, pp. 995–998.

Chemical Abstracts, vol. 74, No. 14, Apr. 5, 1971, Columbus, Ohio, U.S.; abstract No. 65535a, D. Simov, Et al.: "Preparation of azo dyes containing amobile chlorine atom in the benzene ring" p. 81: XP002083055 see abstract & IZV. OTD. KHIM. NAUKI, BULG. AKAD. NAUK, vol. 3, No. 1, 1970, pp. 69–82.

I.C. Poppoff, et al.: "Antimalarial agents. 8. Ring–substituted bis–(4–aminophenyl) sulphones and their precursors" *Journal of Medicinal Chemistry*, vol. 14, No. 12, Dec. 1971, pp. 1166–1169, XP002083052 Washington, DC, U.S. see compounds V, VIII,X, XI, XIII, XVII, XIX, XXVIII, XXXII, XXXVI–XXXVIII, XLI, XLII, XLIV, XLV.

G.E. Chivers, et al.: "Studies in the chemistry of polyhalogenobenzene compounds. The synthesis and reactivity of 2,3,5,6– and 2,3,4,5–tetrachlorobenzenesulphonyl chlorides and related compounds"; *Australian Journal of Chemistry*, vol. 29, No. 7, Jul. 1976, pp. 1572–1582, XP002083174, Melbourne, AU.

P.G. DeBenedetti, et al.; "Quantitative structure–activity analysis in dihydropteroate synghase inhibition by sulphones. Comparison with sulphanilamides" *Journal of Medicinal Chemistry*, vol. 30, No. 3, Mar. 1987, pp. 459–464. XP002083053 Washington, DC, U.S..

V.N. Babushkin, et al.: "Influence of substituents on the frequency of stretching vibrations of sulphur–containing bridging groups in diphenyl systems" *Journal of General Chemistry of the USSR*, vol. 58, No. 7, pt 2, Jul. 1988., pp. 1457–1460. XP002083054 New York, U.S.

Bai, et al.; "Identification of the cystein Residue of β–Tubulin Alkylated by the Antimitotic Agent 2,4–Dichlorobenzyl Thiocyanate, Facilitated by Separationof the Protein subunits of Tubulin by Hydrophobic column chromatography"; *Biochemistry* 1989, vol. 28, pp 5606–5612.

Fadeeva, V.P., et al., "Gas–chromatographic separation of sulfur–and fluorine–containing pyrolysis products", *Chemical Abstracts*, 76:(5) (Jan. 31, 1972).

Gerig et al., "Aromatic Ring Dynamics in a Carbonic Anhydrase–Inhibitor Complex", *Journal of the Chemical Society Chemical Communications*, No. 6, pp 482–484 (1987).

Luduena, E.F., et al. Interaction of Ethacrynic Acid with Bovine Brain Tubulin, *Biochemical Pharmacology*, 47:(9) 1677–1681 (Apr. 29, 1994).

March, Advanced Organic Chemistry, 4th Edition, 1992 p. 497.

Yoshimoto et al., "Correlation Analysis of Baker's Studies . . . ", J. Med. Chem, 19:(1) 71–98 (1976).

Taniuch et al., Chem Abstract. 82:126077, 1975.

Medina et al., "Novel Antineoplastic Agents with Efficacy Against Multidrug Resistant Tumor Cell Lines", *Bioorg. Med. Chem lett.*, 8(9), pp 2653–2656 (1998).

U.S. patent application Ser. No. 08/605,431, Flygare et al., filed Feb. 22, 1998.

Eli Lilly and Company; "Gemzar (Gemcitabine HCl) for Injection" PV 4061 AMP Eli Lilly and Company: Indianapolis, IN 46285, USA 20pages (2003).

\* cited by examiner

Efficacy of Compound 2 or Paclitaxel Either Alone or in Combination Against MX-1 Human Mammary Tumor Xenografts in Athymic Nude Mice FIGURE 3
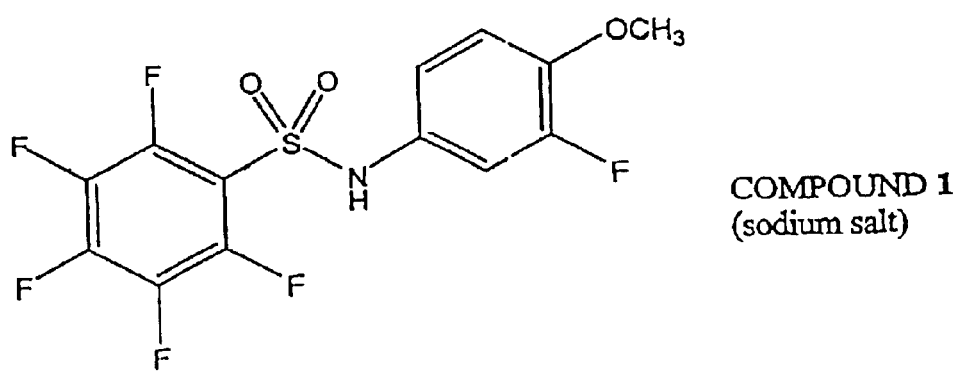
COMPOUND 1
(sodium salt)
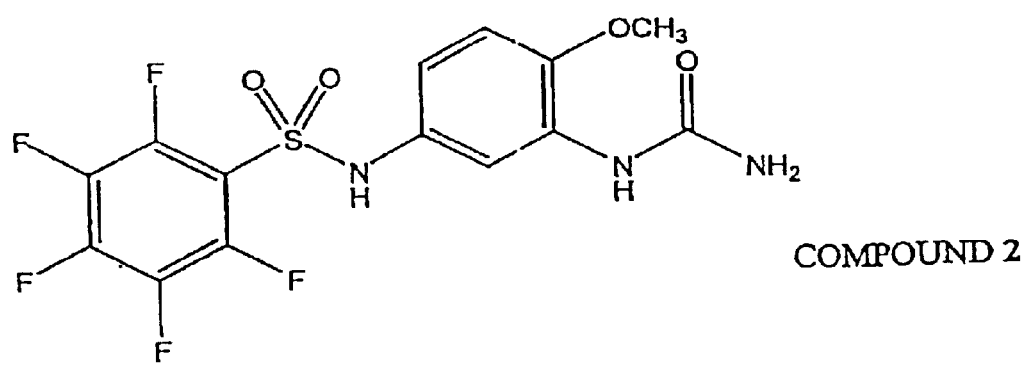
COMPOUND 2
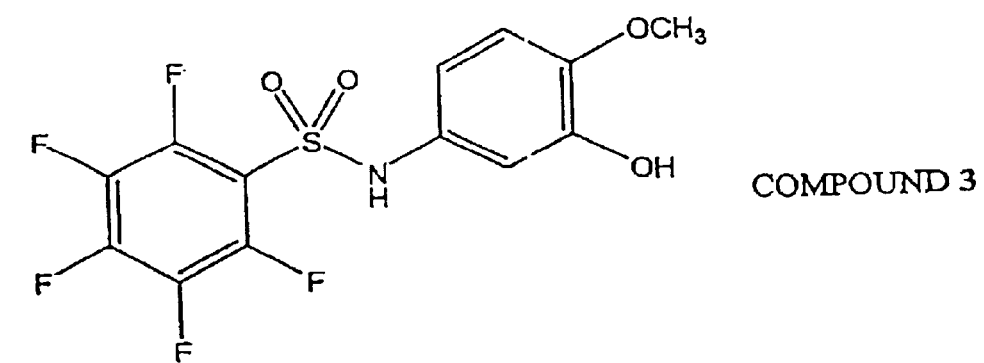
COMPOUND 3

COMBINATION THERAPY USING PENTAFLUOROBENZENESULFONAMIDES AND ANTINEOPLASTIC AGENTS

CROSS-REFERENCES TO RELATED APPLICATIONS

This application claims the benefit of U.S. Ser. No. 60/245,878, filed Nov. 3, 2000, the disclosure of which is incorporated herein by reference. Also, this application is related in technology to application Ser. No. 09/627,041, filed Jul. 27, 2000, and now U.S. Pat. No. 6,335,628.

STATEMENT AS TO RIGHTS TO INVENTIONS MADE UNDER FEDERALLY SPONSORED RESEARCH AND DEVELOPMENT

Not applicable

BACKGROUND OF THE INVENTION

1. Field of the Invention

The present invention relates to combinations of pentafluorobenzenesulfonamides and various other chemotherapeutic agents that are capable of inhibiting abnormal cell proliferation.

2. Background

Cancer is a generic name for a wide range of cellular malignancies characterized by unregulated growth, lack of differentiation, and the ability to invade local tissues and metastasize. These neoplastic malignancies affect, with various degrees of prevalence, every tissue and organ in the body. A multitude of therapeutic agents have been developed over the past few decades for the treatment of various types of cancer. The most commonly used types of anticancer agents include: DNA-alkylating agents (e.g., cyclophosphamide, ifosfamide), antimetabolites (e.g., methotrexate, a folate antagonist, and 5-fluorouracil, a pyrimidine antagonist), microtubule disrupters (e.g., vincristine, vinblastine, paclitaxel), DNA intercalators (e.g., doxorubicin, daunomycin), and hormone therapy (e.g., tamoxifen, flutamide). The ideal antineoplastic drug would kill cancer cells selectively, with a wide therapeutic index relative to its toxicity towards non-malignant cells. It would also retain its efficacy against malignant cells, even after prolonged exposure to the drug. Unfortunately, none of the current chemotherapies possess an ideal profile. Most possess very narrow therapeutic indexes and, in practically every instance, cancerous cells exposed to slightly sublethal concentrations of a chemotherapeutic agent will develop resistance to such an agent, and quite often cross-resistance to several other antineoplastic agents.

The development of new anticancer agents has given rise to new treatment regimens and new combinations that are proving more effective in combating this disease.

Accordingly, it is one object of the present invention to provide compositions which directly or indirectly are toxic to actively dividing cells and are useful in the treatment of cancer.

A further object of the present invention is to provide methods for killing actively proliferating cells, such as cancerous, bacterial, or epithelial cells, and treating all types of cancers, and generally proliferative conditions. A further object is to provide methods for treating other medical conditions characterized by the presence of rapidly proliferating cells, such as psoriasis and other skin disorders.

Additional objects, features and advantages will become apparent to those skilled in the art from the following description and claims.

SUMMARY OF THE INVENTION

In one aspect, the present invention provides compositions useful for the treatment of cancer and other diseases associated with abnormal cell proliferation. The compositions comprise an antineoplastic agent, including but not limited to prodrugs thereof, pharmaceutically acceptable salts of these agents and a compound having the formula:

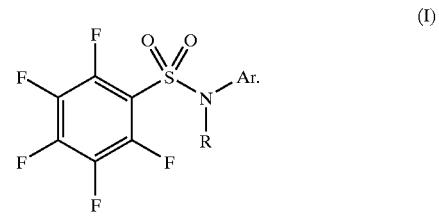

(I)

In the formula above, the letter R represents a hydrogen, substituted or unsubstituted $(C_1-C_{10})$alkyl, or substituted or unsubstituted $(C_3-C_6)$alkenyl. The symbol Ar represents a substituted or unsubstituted aryl group or a substituted or unsubstituted heteroaryl group.

Suitable antineoplastic or antiproliferative agents include, but are not limited to, DNA-alkylating agents (e.g., cyclophosphamide, BCNU, busulfan and temozolamide), antimetabolites, antifolates and other inhibitors of DNA synthesis (e.g., methotrexate, 5-fluorouracil, gemcitabine), microtubule disruptors (e.g., vincristine, vinorelbine, paclitaxel, docetaxel), DNA intercalators (e.g., doxorubicin, daunomycin), hormone agents (e.g., tamoxifen, flutamide), topoisomerase I/II inhibitors and DNA repair agents (e.g., hydroxyurea, camptothecin, etoposide), growth factor receptor kinase inhibitors (e.g., AG1478 and AG1296), biological response modifiers (including cytokines such as interferon α and growth factor inhibitors), antiangiogenic and antivascular agents (e.g., combretastatin A-4), and other agents such as immunoconjugates (e.g., trasuzamab) and antisense oligonucleotides.

The compositions will, in some embodiments, contain a pharmaceutically acceptable carrier or diluent.

In another aspect, the present invention provides methods for the treatment of cancer and other proliferative disorders using the compositions provided above, or using the components in a sequential or simultaneous administration.

BRIEF DESCRIPTION OF THE DRAWINGS

FIG. 3 provides the structures of Compound 1, Compound 2 and Compound 3.

DESCRIPTION OF THE SPECIFIC EMBODIMENTS

Definitions

Figure 1:
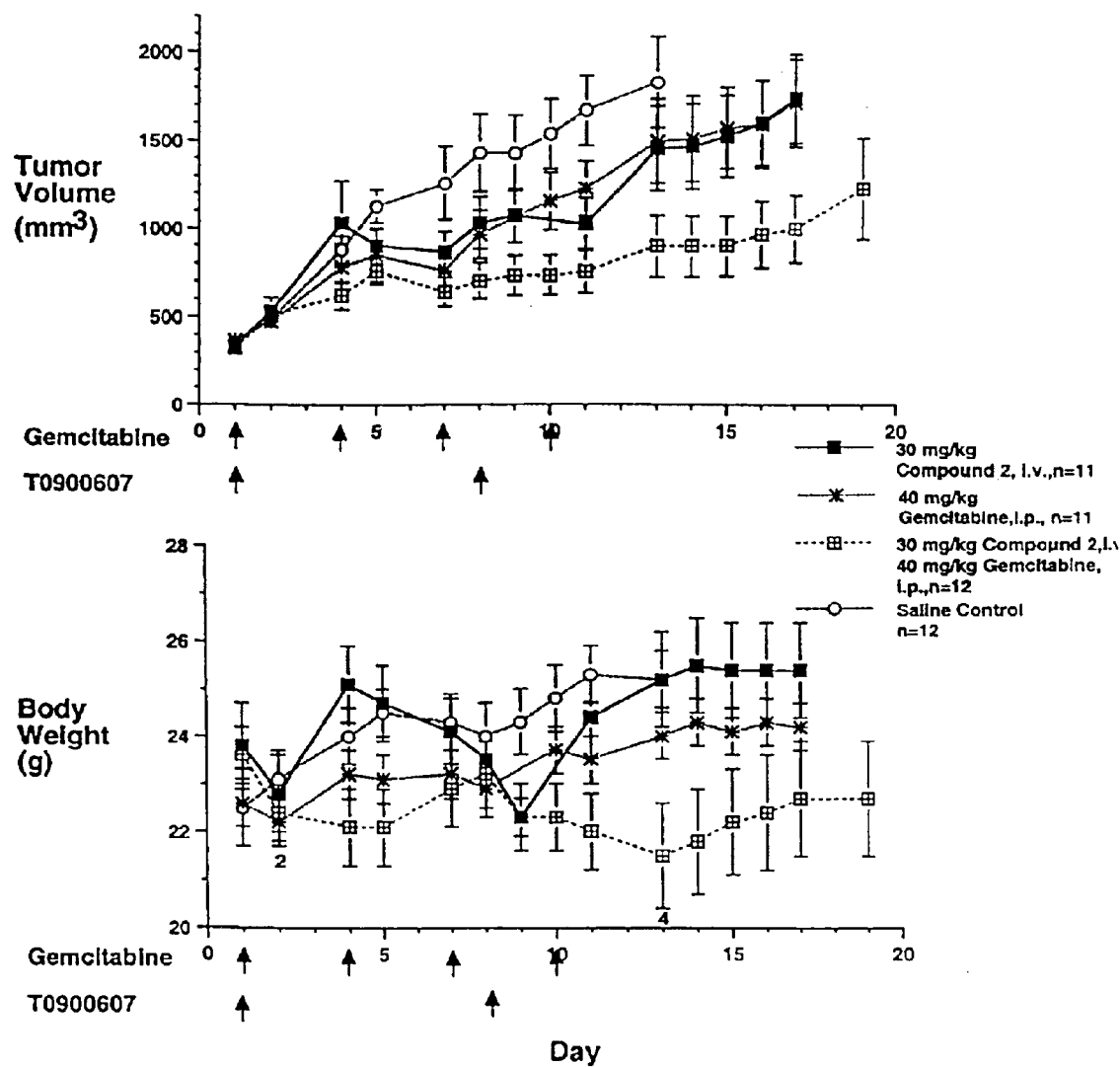
FIG. 1 is a graph which illustrates the effects of Compound 2 with gemcitabine in the treatment of MX-1 human mammary tumor xenografts in athymic nude mice, using suboptimal doses of each of the agents.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl." Alkyl groups which are limited to hydrocarbon groups are termed "homoalkyl".

The term "alkylene" by itself or as part of another substituent means a divalent radical derived from an alkane, as exemplified by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo ($C_1$–$C_4$)alkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R"', —OC(O)R', —C(O)R', —CO$_2$R', —CONR"R", —OC(O)NR'R", —NR"C(O)R', —NR'—C(O)NR"R"', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R"' each independently refer to hydrogen, unsubstituted ($C_1$–$C_8$)alkyl and heteroalkyl, unsubstituted aryl, aryl substituted with 1–3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2C_2$) and acyl (e.g., —C(O)$CH_3$, —C(O)$CF_3$, —C(O)$CH_2OCH_3$, and the like).

Similarly, substituents for the aryl and heteroaryl groups are varied and are selected from: -halogen, —OR', —$OPO_3H_2$, —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', ,—NR'—C(O)NR"R'", —NH—C($NH_2$)=NH, —NR'C($NH_2$)=NH, —NH—C($NH_2$)=NR', —S(O)R', —S(O)$_2$R', —S(O)$_2$NR'R", —$N_3$, —CH(Ph)$_2$, perfluoro($C_1$-$C_4$)alkoxy, and perfluoro($C_1$-$C_4$) alkyl, in a number ranging from zero to the total number of open valences on the aromatic ring system; and where R', R"and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula —T—C(O)—(CH$_2$)$_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula —A—(CH$_2$)$_r$—B—, wherein A and B are independently —$CH_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I ) or carbon-14 ($^{14}$C). All isotopic variations of the compounds of the present invention, whether radioactive or not, are intended to be encompassed within the scope of the present invention.

General

A number of arylsulfonamides have recently been described for the treatment of disorders and conditions arising from abnormal cell proliferation and from elevated plasma cholesterol levels. See, for example, PCT publications WO 97/30677, WO 98/05315 and WO 99/10320. Representative of this new class of anticancer agents are the pentafluorobenzenesulfonamides described in WO 98/05315. These agents are thought to exert their effect by binding to β-tubulin and disrupting microtubule formation. See, Medina et al., Bioorganic & Med. Chem. Letters, 8(19):2653–56 (1998).

Still other pentafluorobenzenesulfonamides have been described in co-pending application Ser. Nos. 60/090,681 filed Jun. 25, 1998 and 09/336,062 filed Jun. 18, 1999, now abandoned; Ser. Nos. 60/093,570 filed Jul. 20, 1998 and 09/353,976 filed Jul. 15, 1999; and Ser No. 60/100,888 filed Sep. 23, 1998, now U.S. Pat. No. 6,153,585.

Clinical trials are in progress to evaluate the pentafluorobenzene-sulfonamide class of compounds for the treatment of cancer, both alone and in combination with other agents. The concept of combination therapy is well exploited in current medical practice. Treatment of a pathology by combining two or more agents that target the same pathogen or biochemical pathway sometimes results in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect can be synergistic (the efficacy of the combination is greater than the sum of the effects of each drug given alone). In real medical practice, it is often quite difficult to determine if drug combinations are additive or synergistic.

DESCRIPTION OF THE EMBODIMENTS

Compositions

In one aspect, the present invention provides compositions comprising an antineoplastic agent and a compound having the formula:

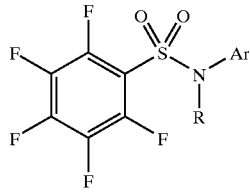

(I)

or a pharmaceutically acceptable salt thereof.

In the formula above, the letter R represents a hydrogen, substituted or unsubstituted $(C_1-C_{10})$alkyl, or substituted or unsubstituted $(C_3-C_6)$alkenyl. The symbol Ar represents a substituted or unsubstituted aryl group or a substituted or unsubstituted heteroaryl group.

In preferred embodiments, R represents a hydrogen or substituted or unsubstituted $(C_1-C_4)$alkyl group, more preferably hydrogen, methyl or ethyl.

Also preferred are those embodiments in which Ar represents a substituted aryl or substituted heteroaryl group, preferably those having a single ring (e.g., substituted phenyl, substituted pyridyl and substituted pyrimidyl). Particularly preferred embodiments are those in which Ar is substituted phenyl. For those embodiments in which Ar is substituted phenyl, the substituents will typically be present in a number of from one to three. Preferred substituents are selected from -halogen, —OR', —OPO$_3$H$_2$, —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', perfluoro$(C_1-C_4)$alkoxy, and perfluoro$(C_1-C_4)$alkyl, where R', R"and R'" are independently selected from hydrogen, $(C_1-C_4)$alkyl, unsubstituted aryl and heteroaryl, (unsubstituted aryl)-$(C_1-C_4)$alkyl, and (unsubstituted aryl)oxy-$(C_1-C_4)$alkyl. Particularly preferred substituents are halogen, $(C_1-C_4)$alkyl, —OR', —OPO$_3$H$_2$, —OC(O)R', —NR'R", —CO$_2$R', —CONR'R", —C(O)R', —OC(O)NR'R", —NR"C(O)R', —NR"C(O)$_2$R', —NR'—C(O)NR"R'", perfluoro$(C_1-C_4)$alkoxy, and perfluoro$(C_1-C_4)$alkyl, in which R', R"and R'" are hydrogen or $(C_1-C_4)$alkyl. Still further preferred are those embodiments in which Ar is selected from:

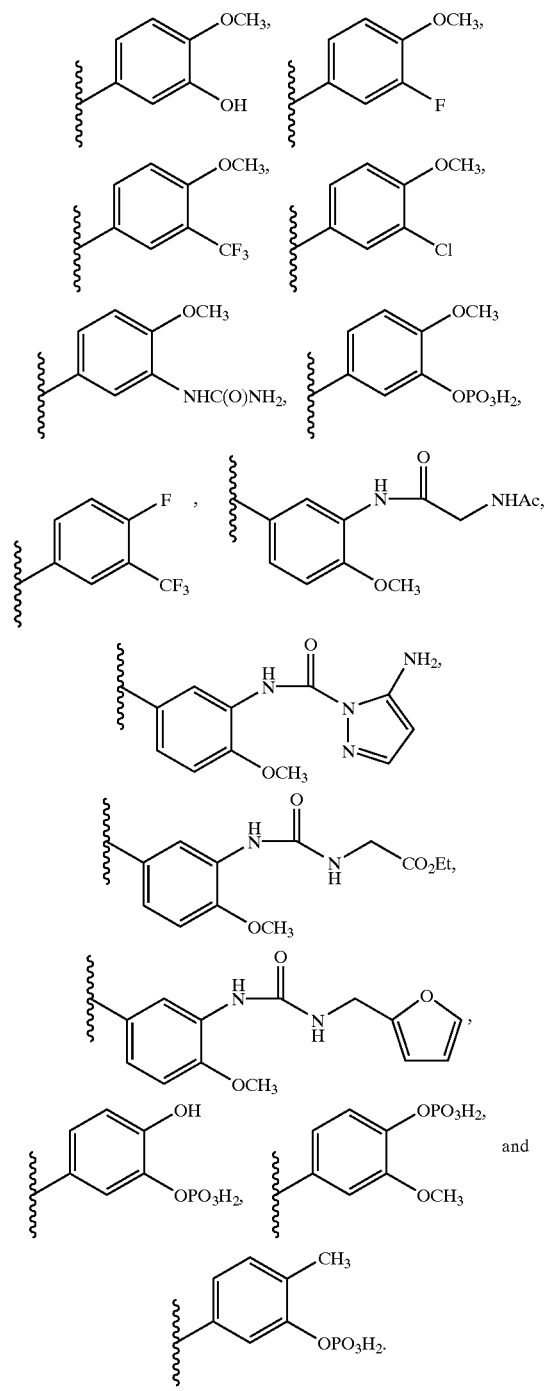

In the most preferred embodiments of the invention, the pentafluorobenzenesulfonamide compound used in the composition is selected from:

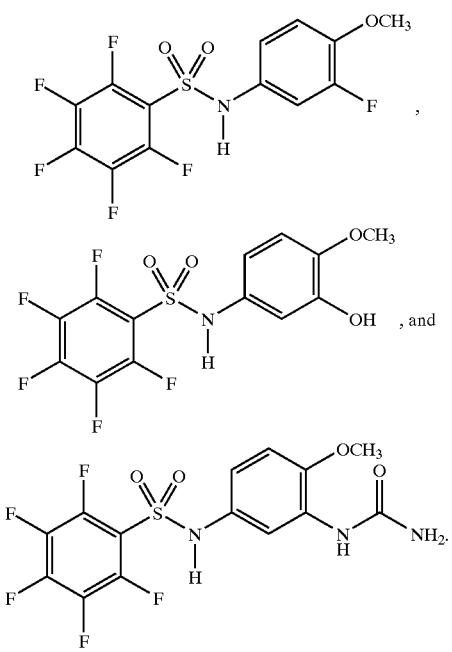

The compositions of the present invention will further comprise an antineoplastic agent. Suitable antineoplastic or antiproliferative agents include, but are not limited to, DNA-alkylating agents (e.g., cyclophosphamide, BCNU, busulfan and temozolamide), antimetabolites, antifolates and other inhibitors of DNA synthesis (e.g., methotrexate, 5-fluorouracil, gemcitabine), microtubule disruptors (e.g., vincristine, vinorelbine, paclitaxel, docetaxel), DNA intercalators (e.g., doxorubicin, daunomycin), hormone agents (e.g., tamoxifen, flutamide), topoisomerase I/II inhibitors and DNA repair agents (e.g., hydroxyurea, camptothecin, etoposide), growth factor receptor kinase inhibitors (e.g., AG1478 and AG1296), biological response modifiers (including cytokines such as interferon a and growth factor inhibitors), antiangiogenic and antivascular agents (e.g., combretastatin A-4), and other agents such as immunoconjugates (e.g., trasuzamab) and antisense oligonucleotides. Thus, in one embodiment of the present invention, the composition comprises a pentafluorobenzenesulfonamide as defined herein and an antineoplastic agent selected from the group consisting of DNA-alkylating agents, antimetabolites, antifolates and other inhibitors of DNA synthesis, microtubule disruptors, DNA intercalators, hormone agents, topoisomerase I/II inhibitors, DNA repair agents, growth factor receptor kinase inhibitors, biological response modifiers, antiangiogenic and antivascular agents, immunoconjugates and antisense oligonucleotides.

In another embodiment, the composition comprises a pentafluorobenzenesulfonamide as defined herein and an antineoplastic agent selected from the group consisting of cyclophosphamide, BCNU (carmustine), busulfan, temozolomide, UFT, capecitabine, gemcitabine, cytarabine, improsulfan, piposulfan, benzodepa, carboquone, meturedepa, uredepa, altretamine, triethylenemelamine, triethylenephosphoramide, triethylenethiophosphoramide, trimethylolmelamine, chlorambucil, estramustine, ifosfamide, novembrichin, prednimustine, uracil mustard, dacarbazine, fluorouracil, methotrexate, mercaptopurine, thioguanine, vinblastine, vincristine, vinorelbine, vindesine, etoposide, teniposide, daunorubicin, doxorubicin, epirubicin, mitomycin, dactinomycin, daunomycin, plicamycin, bleomycin, L-asparaginase, camptothecin, hydroxyurea, procarbazine, mitotane, aminoglutethimide, tamoxifen, flutamide, mitoxantrone, paclitaxel, docetaxol, and thiotepa.

In preferred embodiments, the antineoplastic agent is gemcitabine or paclitaxel.

As noted above, in the most preferred embodiments of the present invention, the pentafluorobenzenesulfonamide compound used in the compositions is selected from Compound 1, Compound 2, and Compound 3 (see FIG. 3). While an understanding of the mechanism by which these compounds are metabolized is not necessary in order to practice the present invention, it is believed that glutathione conjugation plays a major role. Some preferred embodiments of the invention entail the use of compositions comprising Compound 1, Compound 2, or Compound 3 with an antineoplastic agent whose metabolism also is dependent, at least in part, on the formation of a glutathione conjugate (which may include, e.g., BCNU, cyclophosphamide, and thiotepa). Determination of glutathione metabolism can be accomplished according to standard methods known to those of skill in the art (see, e.g., Mannervik and Widersten in ADV. IN DRUG METAB. IN MAN, G. M. Pacifici and G. N. Fracchis, eds., European Commission, Luxemburg: 407–459 (1995), using glutathione transferases available from commercial sources such as PanVera, product nos. P2175, P2192 and P2177, and Research Diagnostics). Enhanced efficacy may be observed with such combinations due to competition for glutathione metabolism. Depending on the agents involved, this may result in depletion of glutathione levels, delayed metabolism of one or both agents, and increased exposure of the malignant tissue to one or more of the composition's active components.

Methods of Treating Proliferative Disorders

The present invention provides, in another aspect, methods for the treatment of proliferative disorders. In one embodiment, treatment is carried out using a composition comprising each of the two agents described above. In another embodiment, treatment comprises separate administration of one or more antineoplastic agents and a pentafluorophenylsulfonamide of formula I.

i. Combination Composition

In this embodiment of the invention, a composition of two or more agents (described above) is administered to a patient in need of treatment. The amount of each agent will typically be less than an amount that would produce a therapeutic effect if administered alone. The precise method of administration will depend on the patient and the judgment of the clinician, but will preferably be intravenous.

ii. Compositions Used Sequentially (Administer Each Separately)

In this embodiment of the invention, conventional protocols are described for the administration of an antineoplastic agent and compound 1 (as representative of the compounds of formula I). One of skill in the art will understand that various changes can be made by the clinician, depending on the particular agents selected for use and the routes and timing of administration. Thus, the present invention contemplates that the antineoplastic agent and the compounds of formula I can be administered sequentially on the same day, on concurrent days, or up to about 4 weeks apart.

The antineoplastic agent is preferably administered with a single intravenous infusion on day one of compound 1 administration period about four hours after the first day's administration of compound 1. To maintain sufficient hydration, one liter of normal saline with 20 meq KCl/L and 1 gm of magnesium sulfate, at a rate of about 250 ml/hour is administered prior to and after the infusion. Additional fluid may be given to maintain adequate urine output.

The treatment cycle may be continued until a clinical response is achieved or until intolerable side effects are encountered. The dosages of compound 1 and/or antineoplastic agent may be increased with each new treatment cycle, provided intolerable side effects are not encountered. The dosages may also be decreased if intolerable side effects are encountered. It is presently preferred to gradually adjust the dosage of compound 1 while holding the antineoplastic agent dosage constant.

As alluded to previously, certain preferred embodiments of the present invention entail combination therapy involving a pentafluorobenzenesulfonamide compound selected from Compound 1, Compound 2, and Compound 3 (see FIG. 3) and at least one other antineoplastic agent, wherein metabolism of the other antineoplastic agent(s) is dependent, at least in part, on the formation of a glutathione conjugate. In such embodiments, the order of administration may be especially important; that is, the order of administration may result in enhanced efficacy while minimizing adverse effects. In some preferred embodiments, it is preferable to administer Compound 1, Compound 2 or Compound 3 prior to the other antineoplastic agent, while in other preferred embodiments it is advantageous to co-administer the agents.

A common, but tolerable side effect of antineoplastic agent is nausea and vomiting. This can be alleviated by administering an anti-emetic (e.g., Ondansetron®, Granisetron®, Decadron®, Haldol®, Benadryl®, Ativan® and the like).

Of course, other forms of administration of both active ingredients, as they become available, are contemplated, such as by nasal spray, transdermally, by suppository, by sustained release dosage form, by IV injection, etc. Any form of administration will work so long as the proper dosages are delivered without destroying the active ingredient.

The effectiveness of treatment may be determined by controlled clinical trials. Patients having cancer with measurable or evaluable tumors will be included in the study. A measurable tumor is one that can be measured in at least two dimensions such as a lung tumor surrounded by aerated lung, a skin nodule, or a superficial lymph node. An evaluable tumor in one that can be measured in one dimension such as a lung tumor not completely surrounded by aerated lung or a palpable abdominal or soft tissue mass that can be measured in one dimension. Tumor markers which have been shown to be highly correlated with extent of disease will also be considered to provide an evaluable disease, such as PSA for prostate cancer, CA-125 for ovarian cancer, CA-15-3 for breast cancer, etc.

The tumor will be measured or evaluated before and after treatment by whatever means provides the most accurate measurement, such as CT scan, MRI scan, Ultrasonography, etc. New tumors or the lack thereof in previously irradiated fields can also be used to assess the anti-tumor response. The criteria for evaluating response will be similar to that of the WHO Handbook of Reporting Results of Cancer Treatment, WHO Offset Publication 1979, 49-World Health Organization, Geneva. The following results are defined for uni- and bi-dimensionally measurable tumors.

Complete response: Complete disappearance of all clinically detectable malignant disease determined by two observations not less than four weeks apart.

Partial Response: (a) for bidimensionally measurable tumors, a decrease of at least 50% in the sum of the products of the largest perpendicular diameters of all measurable tumors as determined by two observations not less than four weeks apart. (b) for unidimensionally measurable tumors, a decrease by at least 50% in the sum of the largest diameters of all tumors as determined by two observations not less than four weeks apart. In cases where the patient has multiple tumors, It is not necessary for all tumors to have regressed to achieve a partial response as defined herein, but no tumor should have progressed and no new tumor should appear.

Stable disease: (a) for bidimensionally measurable tumors, less than a 50% decrease to less than a 25% increase in the sum of the products of the largest perpendicular diameters of all measurable tumors. (b) for unidimensionally measurable tumors, less than a 50% decrease to less than a 25% increase in the sum of the diameters of all tumors. For (a) and (b) no new tumors should appear.

No clinical response, i.e. progressive disease in defined as an increase of more than 50% in the product of the largest perpendicular diameters for at least one bidimensionally measurable tumor, or an increase of more than 25% in measurable dimension of at least one unidimensionally measurable tumor.

Of course elimination or alleviation of other known signs or symptoms of cancer, especially those listed previously can also be used to evaluate the effectiveness of this invention.

The cancers should be evaluated, i.e. tumors measured, etc., no more than 14 days before the start of the treatment. These cancers should be reevaluated about 28 days after day 1 of administration of the first dose of compound 1 and antineoplastic agent. Twenty eight days after this initial administration another administration period may be performed, and evaluations performed 28 days after the start of this second cycle. The treatment cycles may be continued until a clinical response is achieved or unacceptable toxicity is encountered.

Another aspect of this invention is the treatment of cancer with reduced side effects normally associated with an antineoplastic agent. This objective can be achieved by administration of lower doses of the two active ingredients or by shorter duration of dosing brought about by the synergistic effect of the combination.

EXAMPLES

Figure 2:
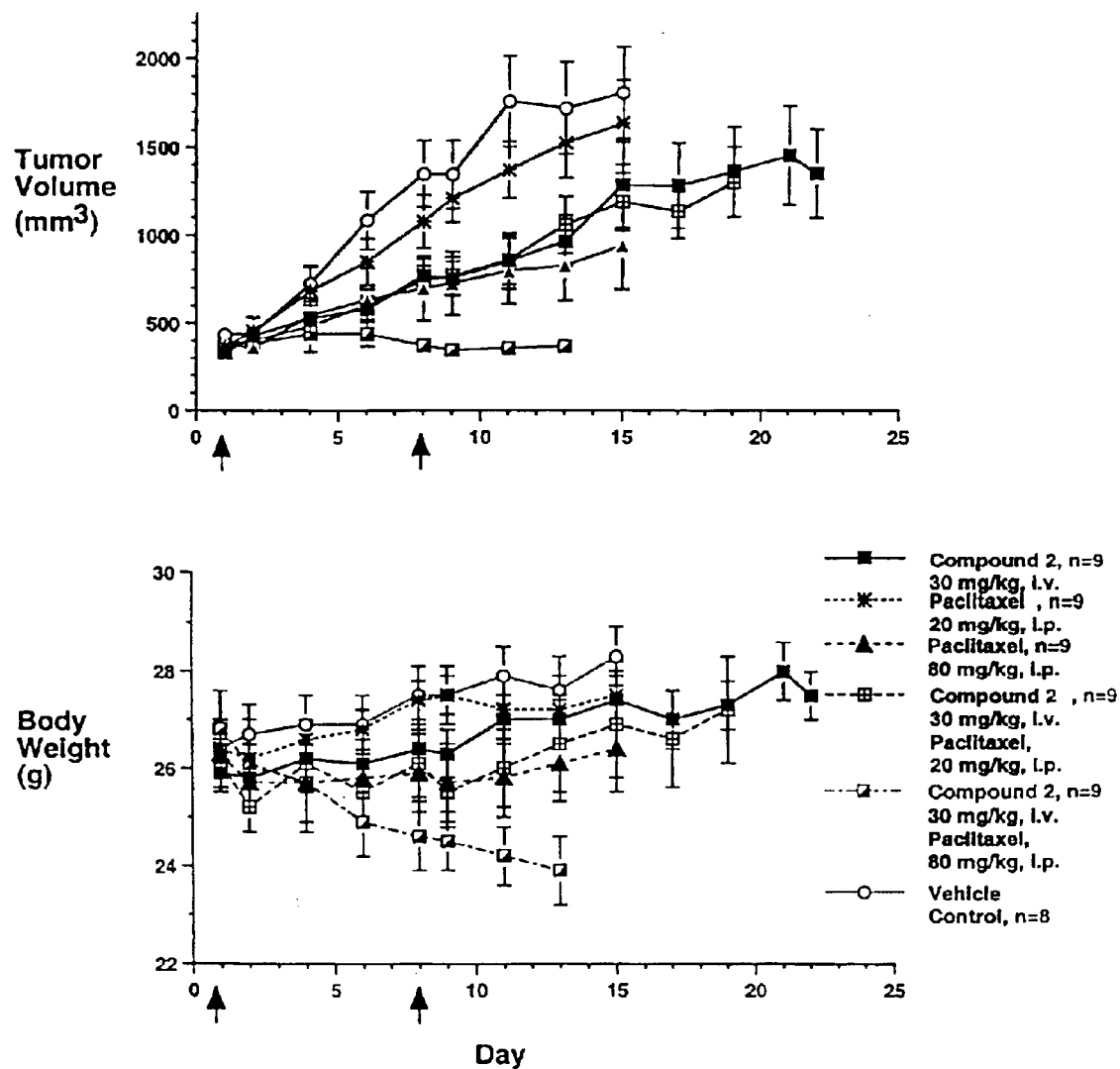
FIG. 2 is a graph which illustrates the effects of Compound 2 with paclitaxel in the treatment of MX-1 human mammary tumor xenografts in athymic nude mice, using suboptimal doses of each of the agents.

FIGS. 1 and 2 illustrate the effect achieved by combining a pentafluorobenzenesulfonamide with gemcitabine or with paclitaxel.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A composition for the treatment of proliferative disorders, said composition comprising an antineoplastic agent selected from the group consisting of paclitaxel and gemcitabine and a compound having the formula:

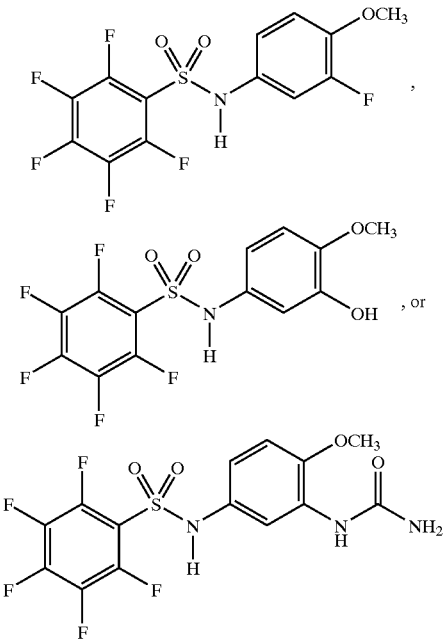

or pharmaceutically acceptable salts thereof.

2. A composition in accordance with claim 1 wherein said antineoplastic agent is paclitaxel.

3. A composition in accordance with claim 1, wherein said antineoplastic agent is gemcitabine.

4. A composition in accordance with claim 1, wherein the formula is

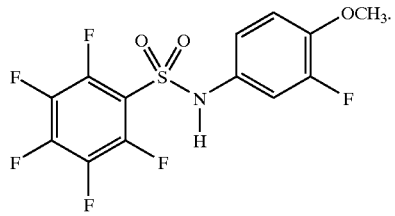

5. A composition in accordance with claim 1, wherein the formula is

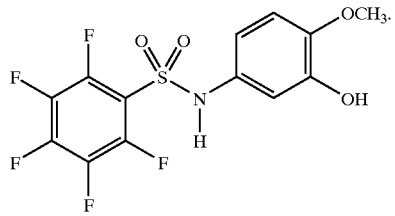

6. A composition in accordance with claim 1, wherein the formula is

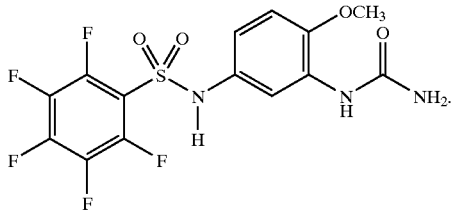

7. A method for the treatment of cancer, comprising administering to a subject in need of such treatment an effective amount of a composition of claim 1.

8. A method in accordance with claim 7, wherein the antineoplastic agent is gemcitabine and the formula is

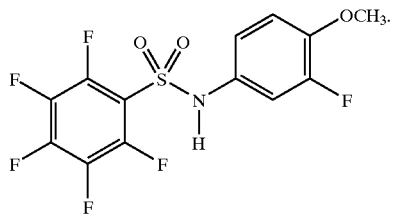

9. A method in accordance with claim 7, wherein said antineoplastic agent is paclitaxel.

10. A method in accordance with claim 7, wherein said antineoplastic agent is gemcitabine.

11. A method for the treatment of cancer, comprising administering to a subject in need of such treatment:
   i) a first amount of an antineoplastic agent selected from the group consisting of paclitaxel and gemcitabine; and
   ii) a second amount of a compound of formula:

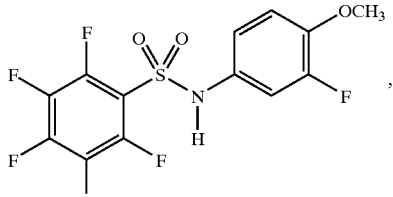

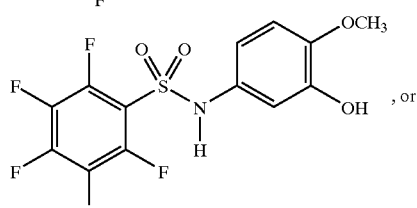

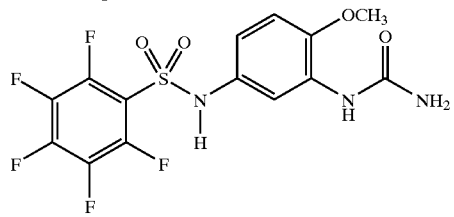

or pharmaceutically acceptable salts thereof;
   wherein said first amount and said second amount, in combination, are effective to treat said cancer.

12. A method in accordance with claim 11, wherein said antineoplastic agent is gemcitabine and said formula is

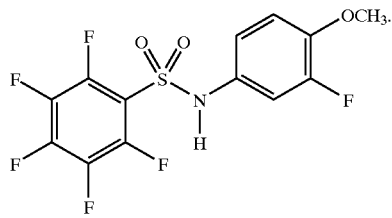

13. A method in accordance with claim 11, wherein said antineoplastic agent is paclitaxel.
14. A method in accordance with claim 11, wherein said antineoplastic agent is gemcitabine.
15. A method in accordance with claim 12, wherein said antineoplastic agent is administered prior to said compound.
16. A method in accordance with claim 12, wherein said antineoplastic agent is administered after said compound.
17. A method in accordance with claim 12, wherein said antineoplastic agent is administered simultaneously with said compound.
18. A method in accordance with claim 11, wherein the cancer is mammary cancer.
19. A method in accordance with claim 11, wherein the subject is human.
20. A method in accordance with claim 7, wherein the subject has mammary cancer.
21. A method in accordance with claim 7, wherein the subject is human.
22. A method in accordance with claim 7, wherein the formula is

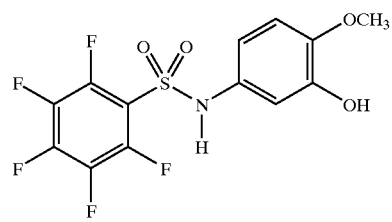

and the antineoplastic agent is gemcitabine.

23. A method in accordance with claim 7, wherein the formula is

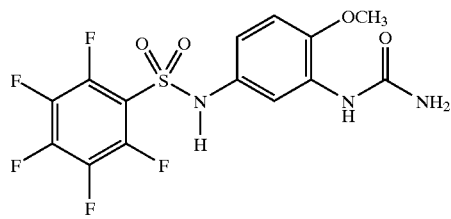

and the antineoplastic agent is gemcitabine.

24. A method in accordance with claim 11, wherein the formula is

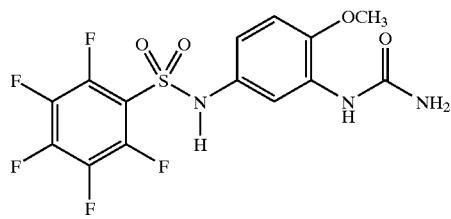

and the antineoplastic agent is gemcitabine.

25. A method in accordance with claim 11, wherein the formula is

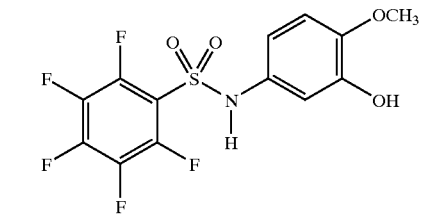

and the antineoplastic agent is gemcitabine.

26. A composition of claim 6, wherein the antineoplastic agent is gemcitabine.

* * * * *